United States Patent [19]

Bückmann

[11] 4,443,594

[45] Apr. 17, 1984

[54] PROCESS FOR THE PRODUCTION OF ADENINE RING SYSTEM CONTAINING CO-ENZYMES BOUND TO MACROMOLECULES

[75] Inventor: Andreas Bückmann, Braunschweig-Stöckheim, Fed. Rep. of Germany

[73] Assignee: Gesellschaft fur biotechnologische forschung mbH (GBF), Braunschweig-Stockholm, Fed. Rep. of Germany

[21] Appl. No.: 300,249

[22] Filed: Sep. 8, 1981

Related U.S. Application Data

[63] Continuation-in-part of Ser. No. 73,317, Sep. 7, 1979, abandoned.

[30] Foreign Application Priority Data

Sep. 22, 1978 [DE] Fed. Rep. of Germany ....... 2841414

[51] Int. Cl.³ .............................................. C07H 19/20
[52] U.S. Cl. ....................................... 536/27; 536/22; 536/25; 536/28; 536/29
[58] Field of Search ...................... 536/22, 25, 28, 29, 536/1, 1.1, 26, 27

[56] References Cited

U.S. PATENT DOCUMENTS

| | | | |
|---|---|---|---|
| 3,985,690 | 10/1976 | Dean et al. | 536/22 |
| 4,008,363 | 2/1977 | Re et al. | 536/28 |
| 4,011,205 | 3/1977 | Dean et al. | 536/22 |
| 4,088,639 | 5/1978 | Zappelli et al. | 536/28 |

FOREIGN PATENT DOCUMENTS 2841414 7/1979 Fed. Rep. of Germany ........ 536/28

OTHER PUBLICATIONS

Zapelli et al., "Chem. Abst.", vol. 83, 1975, p. 55160(w).
Zapelli et al., "Chem. Abst.", vol. 86, 1977, p. 85301(x).

*Primary Examiner*—Johnnie R. Brown
*Attorney, Agent, or Firm*—Bierman, Bierman & Peroff

[57] ABSTRACT

A process for the production of adenine ring system containing co-enzymes bound to a macro-molecular carrier comprising the steps of alkylating an adenine ring system containing co-enzyme in the 1 position with an alkylating agent containing a terminal group capable of reacting with said macro-molecular carrier selected from the group consisting of carboxyl, amine and vinyl, reacting said alkylated co-enzyme with a macromolecular carrier having groups capable of reacting with said terminal groups, subjecting said alkylated co-enzyme bound to a macro-molecular carrier to a Dimroth rearrangement into the $N^6$-form of alkylation, and recovering said adenine ring system containing co-enzyme bound to a macro-molecular carrier.

3 Claims, 1 Drawing Figure

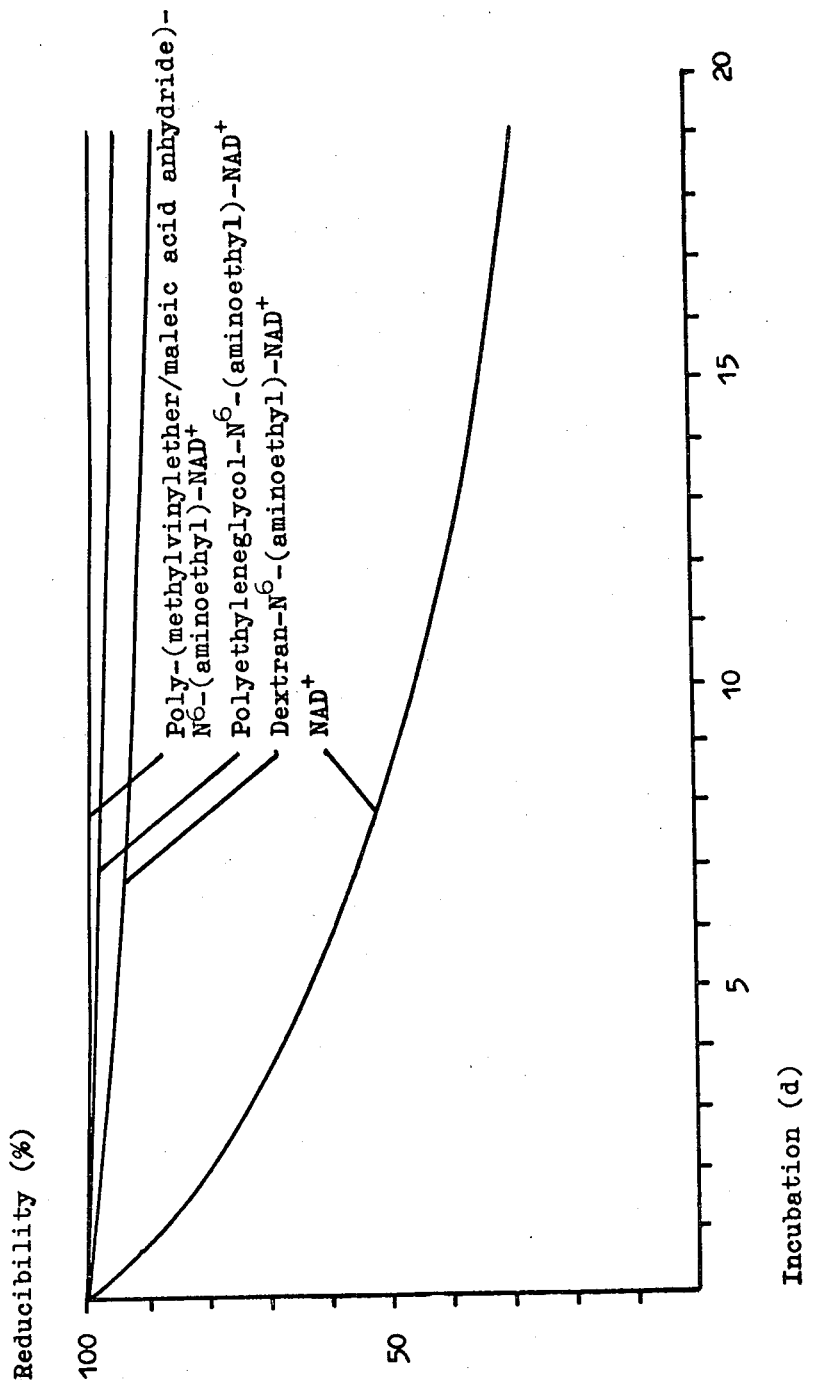

PROCESS FOR THE PRODUCTION OF ADENINE RING SYSTEM CONTAINING CO-ENZYMES BOUND TO MACROMOLECULES

This is a continuation-in-part application of patent application Ser. No. 73,317 (filed on Sept. 7, 1979, now abandoned and assigned to Gesellschaft für Biotechnologische Forschung mbH (GBF)).

BACKGROUND OF THE INVENTION

Co-enzymes and cofactors with an adenine ring system like AMP, ADP, ATP, NAD+/NADH and NADP+/NADPH, which are covalently bound to solid carriers or to soluble polymers, e.g. water soluble polymers, have already been widely used and examined. For example, co-enzymes bound to solid carriers are successfully used as ligands in affinity chromatography. Water soluble polymers with covalently bound co-enzymes are very useful in affinity partitioning. In the case of NAD+/NADH and NADP+/NADPH corresponding compounds can be regenerated and correspondingly used in enzymatical systems with recycling.

When producing co-enzymes covalently bound to macro-molecules and containing an adenine ring system, as is well known, a functional group is first provided at the N-atom in position 6 after which this reactive group is reacted with a macro-molecule.

First of all the adenine ring system is reacted at the N(1)-atom with an alkylating agent bearing an additional functional group which is designed to permit the reaction with the macro-molecule or a chain extension before the reaction with the macro-molecule. Alkylating agents include, for example, halo acids like iodine acetic acid, epoxides like 3.4-epoxy butyric acid, lactones, like propiolactone, or aziridines, like ethylene imine.

In the case of AMP, ADP and ATP the alkylation is immediately succeeded by a Dimroth rearrangement into the $N^6$-form. The Dimroth rearrangement can be immediately followed by the reaction with the macro-molecule or can be followed by the said reaction after a preceding chain extension at the N-atom at position 6. In the case of NAD+ and NADP+ a reduction is carried out before the Dimroth rearrangement and a reoxidation after the Dimroth rearrangement.

The co-enzyme derivatives produced in the same manner can bear, for example, the following functional groups on chains at the N-atom at position 6 for a linking with macro-molecules: carboxylic, amino, or vinyl groups.

For a linking insoluble macro-molecules (carrier, matrices) or soluble, especially water soluble, macro-molecules can be taken into consideration which have one or several functional groups effective for the linking. These macro-molecules may contain such functional groups per se or the said functional groups may be introduced into the macro-molecules, for example according to the bromic cyanide method. (Experts can obtain evidence of the possibility of linking the said macro-molecules by a simple experiment.) Examples for macro-molecules which can be used are: dextrans, polyetherpolyols like polyethyleneglycol, polyethylene-imines, polyacrylamides, co-polymers like poly-(methylvinylether/maleic acid anhydride), agarose, glass, cellulose and derivatives of the said macro-molecules; cf. Lowe, TIBS, 134 (1978) and Mosbach, Advances in Enzymology, 46 (1978) 205 to 278.

In the case of the known processes mentioned, the resulting yield after the Dimroth rearrangement (and after an optionally succeeding chain extension at the N-atom at position 6) has not so far proved satisfactory. The following Table lists yields in the range of merely 12 to 40% for (a) prior art.

(a) Prior Art

Yields (%) after alkylation and Dimroth rearrangement and before coupling with macro-molecules

|  | ATP | ADP | AMP | NAD+ | NADP+ |
|---|---|---|---|---|---|
| Lindberg et al., Eur. J. Biochem., 53, 481–486 (1975) | 40+ | 40+ | 40+ | | |
| Lindberg et al., Eur. J. Biochem., 40, 187–193 (1973) | | | | 23 21+ | |
| Zappelli et al., Eur. J. Biochem., 54, 475–482 (1975) | | | | 20+ | |
| Schmidt et al., Eur. J. Biochem., 67, 295–302 (1976) | | | | 20 | |
| Lowe et al., Eur. J. Biochem., 49, 511–520 (1974) | | | | | 15 to 25 12 to 20+ |

+After extension of the chain at the N—atom at position 6

(b) Invention

Estimated Yields 1 (%) after alkylation, coupling with macro-molecules and Dimroth rearrangement; since the coupling with macromolecules and the Dimroth rearrangement are accompanied by hardly any yield loss, the rearrangement products can be practically obtained with the yield of the co-enzymes alkylated at position 1.

| ATP | ADP | AMP | NAD+ | NADP+ |
|---|---|---|---|---|
| 87 | — | 89 | 60 70 | 70 |

Remarks:
Yields are calculated as follows:

$$\text{Yield (\%)} = \frac{\text{Amount of free coenzyme analogue (before coupling)}}{\text{Starting amount of unmodified coenzyme}} \times 100$$

1: Assumed 100% recycling and reuse of not coupled pure N(1)-(Aminoethyl)-NAD+ or the N(1)-(Aminoethyl) derivatives of NADP+, AMP, ATP and their by-products It is an object of the invention to provide a process for the production of co-enzymes bound to soluble macromolecules or unsoluble macromolecules or carriers and containing an adenine ring system in which the adenine ring system is alkylated at position 1, the alkylated co-enzyme (optionally with a preceding reduction and succeeding reoxidation) is subjected to a Dimroth rearrangement (and optionally to an extension of the alkylene chain introduced by the alkylation) and added to a macro-molecule or a carrier whereby better yields can be obtained. The process according to the invention is characterized in that first of all the alkylation is carried out, then the optional chain extension, then the addition to the macro-molecule and finally the Dimroth rearrangement.

DESCRIPTION OF THE INVENTION

AMP, ADP, ATP, NAD+ and NADP+ each substituted at position 1 can be obtained with yields of about 60 to 90% depending on the reaction time. These derivatives can then be purified. According to the invention the resulting derivatives substituted at position 1 are added to macro-molecules or carriers (briefly: macro-molecules) after which the resulting macro-molecule derivatives can be separated from the unreacted compounds substituted at position 1; these compounds can then be used again. That means, that according to the invention the Dimroth rearrangement is only carried out after this step and is preceded in the case of the NAD+ and NADP+ derivatives by a reduction and may be followed in these cases by a reoxidation. Since the Dimroth rearrangement is accompanied by hardly any yield loss, the rearrangement products can be practically obtained with the yield of the starting products substituted at position 1, i.e. with a yield of about 60 to 90%.

The disclosure of the invention in question comprises the contents of the publications mentioned, especially with respect to the optional reduction and reoxidation in connection with the Dimroth rearrangement.

In connection with this invention the following discovery was made. The chemical stability of co-enzymes is an essential parameter in enzymatical processes in the presence of co-enzymes. For example, NADH is fairly stable in an aqueous solution at moderately basic conditions (pH $\geq 7.0$ and $\leq 9.0$), which are necessary for an optimal catalytic activity of dehydrogenases. On the other hand free NAD+ shows a remarkable loss of activity at room temperature when used in the mentioned pH range.

According to the invention it was found out that NAD+ can be stabilized against a base catalyzed decomposition in a moderately basic medium, if the NAD+ is covalently bound to macro-molecules. A pH range of 6.0 to 11.0, especially 7.0 to 9.0 is preferred where dehydrogenases show their optimal catalytic activity.

Now the invention is explained by examples.

EXAMPLE 1

Production of dextran-N$^6$-(aminoethyl)-NAD+

A. Production of N(1)-(aminoethyl)-NAD+

7 g NAD+ (quality II by Boehringer) were dissolved in 12 ml distilled water. 1 ml ethylene imine (Fluka) was slowly added thereto and a pH of 4.3 to 4.7 was maintained with 70% perchloric acid (total volume 19 ml). The reaction mixture was stirred for 3 days at 20° C. at a pH of 4.3 to 4.7 (adjustment with 70% perchloric acid). The reaction was enzymatically followed with brewer's yeast alcohol dehydrogenase (compared with the reduction of N(1)-(aminoethyl)-NAD+ the enzymatical reduction of NAD+ is very fast). The reaction mixture was diluted with distilled water to 100 ml and an eight to ten-fold quantity of cold ethanol (0° C.) was added to it. The resulting precipitate was centrifuged; thereby the nucleotides were separated while the ethylene imine remained dissolved. After centrifuging for one and a half hours the ethanol supernatants were discarded. The precipitate was washed in cold ethanol and centrifuged once again. The precipitates were dissolved in 250 ml distilled water and the solution was lyophilized overnight. (It is possible to store dry material without any decomposition at +4° C. in a dry atmosphere.)

The lyophilized reaction mixture obtained with 7 g NAD+ was dissolved in 600 ml water and put onto a cation exchanger at a pH of 5.75 (70×2.5 cm, 200 to 400 mesh, Biorex 70, Biorad) the cation exchanger having been brought to equilibrium by an 0.015 M sodium citrate solution having a pH of 5.75. After the application the NAD+ fraction was elutriated with an 0.015 M sodium citrate solution having a pH of 5.75. Immediately after the NAD+ had passed through an elution with water was started the pH of which had been adjusted with 1 N chloric acid to 3.0 (10 column volumes). It was possible to eluate N(1)-(aminoethyl)-NAD+ and the side product with 0.2 M lithium chloride and 0.6 M lithium chloride, respectively, in water at a pH of 3. The fractions were concentrated by flash evaporation and precipitated in cold ethanol four times (20-fold surplus based on the volume) whereby the lithium chloride could be separated, which is easily soluble in ethanol. The products were able to be lyophilized and were stored in a manner as indicated.

The resulting conversions are listed as follows.

| Results of the reaction of NAD+ with ethylene imine (0.53:1 mol) | | | | |
|---|---|---|---|---|
| Duration of Reaction (d) | Conversion (enzymatically determined) | NAD+ | N(1)-(aminoethyl)-NAD+ | Side Product |
| 3 | 65 | 35 | 60 | 5 |
| 4 | 80 | 20 | 70 | 10 |

N(1)-(aminoethyl)-NAD+ and the side product show a positive reaction with ninhydrin (primary amino groups are present); both show a characteristic shoulder in the range of 300 to 310 nm at pH 11.5 (alkylation at position 1 of the adenine ring system). With CN$^-$ a complex is formed having an absorption maximum at 325 nm (oxidized nicotinamide is present). The side product shows a fluorescence at 366 nm (excitation). Both are active when tested with brewer's yeast alcohol dehydrogenase. The correct structure of the side product is unknown.

B. Coupling of N(1)-(aminoethyl)-NAD+ to macro-molecules

N(1)-(aminoethyl)-NAD+ was coupled to carboxylated dextran ($\overline{M}$ 40 000). The carbodiimide method was applied for the coupling according to inter alia Cuatrecasas, J. Biol. Chem., 245, 3059 (1970); the disclosure of this publication is included.

The N(1)-(aminoethyl)-NAD+ polymers of this example and of examples 2 to 3 showed the spectral peaks of the free N(1)-(aminoethyl)-NAD+, i.e. an absorption maximum at 259 nm, a shoulder in the range of 300 to 310 nm at pH 11.5 and with CN$^-$ the absorption of the complex at 325 nm.

C. Production of dextran-N(1)-(aminoethyl)-NADH

The reaction was started with 15 ml dextran-N(1)-(aminoethyl)-NAD+ which had been filtered with a gel filter; the ratio N(1)-(aminoethyl)-NAD+ to dextran was 10 to 1 molecules and the average molecular weight of the dextran was 40,000 Dalton. The concentration was 4.9 mmolar with altogether 73.5 $\mu$mol N(1)-(aminoethyl)-NAD+ based on epsilon$_{259}$=18,500 M$^{-1}$cm$^{-1}$. The compound was reduced with a 10-fold surplus of Na$_2$S$_2$O$_4$ in 5 minutes at 70° C. in the presence of sodium hydrogen carbonate (1%) at a pH ranging from 7.5 to 8.0. 16 ml with a 4.5 mmolar concentration and a total amount of 72 $\mu$mol (calculated as N(1)-(aminoethyl)-NADH) were obtained based on epsilon$_{340}$=6220 M$^{-1}$ cm$^{-1}$.

The main absorption maximum of the produced dextran-N(1)-(aminoethyl)-NADH appeared at 259 nm and a second maximum at 340 nm, which indicated the presence of reduced nicotinamide. Strong absorption in the range of 300 to 310 nm at pH 11.5, which indicated an alkylation at position 1 of the adenine ring system. Absorption at 259 nm/absorption at 340 nm=2.4.→epsilon$_{259}$=±15,000 M$^{-1}$ cm$^{-1}$.

D. Production of dextran-N$^6$-(aminoethyl)-NADH

Oxygen was bubbled through the reaction mixture of step C for 10 minutes in order to oxidize a surplus of Na$_2$S$_2$O$_4$. Then the Dimroth rearrangement was carried out; the reaction mixture was heated to 70° C. at pH 11.0 for 1.25 hours.

Then a gel filtration was carried out in 0.03 M potassium chloride at pH 10 on a column (70×3.5 cm, Sephadex G 50). A concentrating of the fraction of the dextran nucleotide material resulted in 23 ml of a 3.14 mmolar concentrate with altogether 72.2 μmol (calculated as N$^6$-(aminoethyl)-NADH) according to epsilon$_{340}$=6220 M$^{-1}$ cm$^{-1}$.

The main absorption maximum appeared at 267 nm and a second maximum at 340. There was no increase of the absorption in the range of 300 to 310 nm at pH 11.5, which indicated that position 1 was no longer alkylated. Absorption at 267 nm/absorption at 340 nm=3.7.→epsilon$_{267}$=23,000 M$^{-1}$ cm$^{-1}$.

The derivative showed a co-enzymatical activity when tested with dehydrogenases like alanine, alcohol, lactate, glutamate, and maleate dehydrogenases; it was able to be enzymatically oxidized up to more than 95%.

E. Oxidation to dextran-N$^6$-(aminoethyl)-NAD+

9 ml dextran-N$^6$-(aminoethyl)-NADH (6.5 mmolar concentration and total amount of 58.5 μmol; calculated as reduced nucleotide) according to epsilon$_{340}$=6220 M$^{-1}$ cm$^{-1}$) was reacted with 3 ml of an aqueous 2 mmolar riboflavin solution and 3 ml of an 0.5 mmolar potassium phosphate buffer at pH 7.0, room temperature and daylight for 2 hours and oxygen bubbled through the reaction medium.

Then a gel filtration with an 0.03 M potassium chloride solution was carried out on a column (70×3.5 cm, Sephadex G 50) and then a concentration by flash evaporation. 17.5 ml dextran-N$^6$-(aminoethyl)-NAD+ were obtained with a 3.37 mmolar concentration and altogether 59 μmol (calculated as N$^6$-(aminoethyl)-NAD+) according to epsilon$_{267}$=23,000 M$^{-1}$ cm$^{-1}$.

The main absorption maximum appeared at 267 nm and a shoulder was missing in the range of 300 to 310 nm. A complex was obtained with CN$^{-1}$ having a maximum absorption at 325 nm.

The resulting derivative showed a co-enzymatical activity when tested with alcohol, lactate, and formate dehydrogenases. An enzymatical reduction up to 50 to 60% was able to be obtained; this relatively small percent yield is due to an establishment of an equilibrium of the catalyzed reaction.

EXAMPLE 2

Production of polyethyleneglycol-N$^6$-(aminoethyl)-NAD+

A to B. The procedure of steps A to B of Example 1 was applied, however, carboxylated polyethyleneglycol ($\overline{M}$ 6000) was used.

C to E. 12 ml polyethyleneglycol-N(1)-(aminoethyl)-NAD+ were fed with altogether 64 μmol N(1)-(aminoethyl)-NAD+ and a 5.3 mmolar concentration according to epsilon$_{255}$=18,500 M$^{-1}$ cm$^{-1}$. The reduction yielded 13 ml polyethyleneglycol-N(1)-(aminoethyl)-NADH with altogether 60 μmol N(1)-(aminoethyl)-NADH with a 4.61 mmolar concentration according to epsilon$_{340}$=6220 M$^{-1}$ cm$^{-1}$ (absorption at 259 nm/absorption at 340 nm=2.40). After passing oxygen through the reaction medium and a Dimroth rearrangement 20 ml polyethyleneglycol-N$^6$-(aminoethyl)-NADH with altogether 59.8 μmol N$^6$-(aminoethyl)-NADH and a 3 mmolar concentration according to epsilon$_{340}$=6220 M$^{-1}$ cm$^{-1}$ were obtained (absorption at 267 nm/absorption at 340 nm=3.7). An oxidation yielded 26 ml polyethyleneglycol-N$^6$-(aminoethyl)-NAD+ with altogether 54 μmol N$^6$-(aminoethyl)-NAD+ and a 2.0 mmolar concentration based on a 90% enzymatical re-reduction.

EXAMPLE 3

Production of poly-(methylvinylether/maleic acid anhydride)-N$^6$-(aminoethyl)-NAD+

A to B. Steps A to B of example 1 were applied; however, carboxylated poly-(methylvinylether/maleic acid anhydride) ($\overline{M}$ 250 000) was used.

Poly-(methylvinylether/maleic acid anhydride), i.e. (methylvinylether/maleic acid anhydride) polymer, contains anhydride groups which are very reactive with respect to compounds with primary amino groups. Therefore, it is possible to bind N(1)-(aminoethyl)-NAD+ at pH 6.5 to 7.0 and a particular ratio of the monomer to N(1)-(aminoethyl)-NAD+ quantitatively (100%), for example, at a ratio of 10 to 50:1 and 10:50, respectively).

C. to E. 11.8 ml poly-(methylvinylether/maleic acid anhydride)-N(1)-(aminoethyl)-NAD+ were fed with all together 49 μmol N(1)-(aminoethyl)-NAD+ and a 4.15 mmolar concentration according to epsilon$_{259}$=18,500 M$^{-1}$ cm$^{-1}$. A reduction yielded 12 ml poly-(methylvinylether/maleic acid anhydride)-N(1)-(aminoethyl)-NADH with altogether 47 μmol N(1)-(aminoethyl)-NADH and a 3.92 mmolar concentration according to epsilon$_{340}$=6220 M$^{-1}$ cm$^{-1}$ (absorption at 259 nm/absorption at 340 nm=2.45). After passing oxygen through the reaction medium and a Dimroth rearrangement 12.5 ml poly-(methylvinylether/maleic acid anhydride)-N$^6$-(aminoethyl)-NADH were obtained with altogether 43 μmol N$^6$-(aminoethyl)-NADH and a 3.45 mmolar concentration according to epsilon$_{340}$=6220 M$^{-1}$ cm$^{-1}$ (absorption at 267 nm/absorption at 390 nm=3.9 to 4.0). An oxidation yielded 16 ml poly-(methylvinylether/maleic acid anhydride)-N$^6$-(aminoethyl)-NAD+ with altogether 30 μmol N$^6$-(aminoethyl)-NAD+ and a 1.9 mmolar concentration based on a 70% enzymatical re-reduction.

EXAMPLE 4

Stability tests were carried out where NAD+, poly-(methylvinylether/maleic acid anhydride)-N$^6$-(aminoethyl)-NAD+, dextran-N$^6$-(aminoethyl)-NAD+ (average molecular weight of dextran 40,000 Dalton) and polyethyleneglycol-N$^6$-(aminoethyl)-NAD+ (average molecular weight of polyethyleneglycol 6,000) from examples 1 to 3 were incubated at a 1 mmolar nucleotide concentration at pH 9 in 0.1 M Tris/HCl with sodium azide (0.02%; in order to inhibit a possible microbial contamination) at room temperature. The stability was tested by examining the enzymatical reducibility with lactate and alcohol dehydrogenases, respectively. The highest absorption which could be achieved at 340 nm at point O in time was taken for 100%. In addition, in the case of $N^6$-(aminoethyl)-$NAD^+$ bound to polymers a gel filtration was carried out on an analytic column (Sephadex G 50) in order to detect free nucleotide. The conditions were as follows: alcohol dehydrogenase (polyethyleneglycol-$N^6$-(aminoethyl)-$NAD^+$): 0.1 M Tris/HCl (pH 8.0)+EDTA ($10^{-4}$ mol)+semicarbazide ($7 \times 10^{-3}$ mol) ethanol (0.2 mol), addition of brewer's yeast alcohol dehydrogenase; lactate dehydrogenase ($NAD^+$, poly-(methylvinylether/maleic acid anhydride)-$N^6$-(aminoethyl)-$NAD^+$ and dextran-$N^6$-(aminoethyl)-$NAD^+$): 0.1 M Tris/HCl (pH 9.0)+EDTA ($10^{-4}$ mol), lactate (0.1 mol), addition of lactate dehydrogenase.

From the graph (single FIGURE of the drawing) a surprisingly increased stability of $NAD^+$ covalently bound to polymer can be drawn as a function of time. It was not possible to detect any free material having an absorption at 267 nm during a gel filtration even after a long incubation in case of $N^6$-(aminoethyl)-$NAD^+$ bound to polymers.

EXAMPLE 5

Conversion of $NAD^+$ with ethyleneimine to N(1)-(Aminoethyl)-$NAD^+$.

For the reaction conditions see Example 1A. The composition of the reaction mixture after 4 days reacting has been later on determined by scanning at 259 nm with a high speed TLC scanner after thin layer chromatography of a sample on a silica gel-60-$F_{254}$ plate (0.25 mm) using the solvent system isobuturic acid/25% aqueous $NH_3/H_2O$, 66/1/33, (v/v/v). Formerly the composition of the reaction mixture was determined by analytical ion exchange on a small column.

After 4 days reacting a typical composition is:
15% $NAD^+$ (not converted)
75% N(1)-(Aminoethyl)-$NAD^+$
10% By-product (ninhydrine positive reaction (—$NH_2$ present), N(1)-alkyl spectral characteristics and coenzymatically active).

After preparative ion exchange of the reaction mixture from 7 g $NAD^+$, 5.2 g N(1)-(Aminoethyl)-$NAD^+$, yield 75% and 0.56 g by-product, yield 8%, were obtained.

The overall yield for the synthesis of polymer-bound $N^6$-(Aminoethyl)-NADH will be in the same range as the yield of the purification of N(1)-(Aminoethyl)-$NAD^+$ since:

1. The coupling procedure of pure N(1)-(Aminoethyl)-$NAD^+$ to carboxylated water-soluble polymers can be carried out without any loss of this $NAD^+$-derivative, because non-coupled N(1)-(Aminoethyl)-$NAD^+$ can be recycled by gel filtration and used again for further attachment.
2. Also the loss due to hydrolysis of the amide bonds under conditions of the reduction and the Dimroth rearrangement was almost negligible (1–4% generally).

So the yield for the synthesis of polymer-bound $N^6$-(Aminoethyl)-NADH will be in the range 70–74%. To obtain polymer-bound-$N^6$-(Aminoethyl)-$NAD^+$ the best procedure is enzymatically with alcoholdehydrogenase from yeast as catalyst and acetaldehyde as substrate (also here almost no loss of coenzyme material). Polymer-bound $N^6$-(Aminoethyl)-$NAD^+$ was obtained according to the following procedures.

Synthesis of polyethylene glycol-$N^6$-(2-Aminoethyl)-$NAD^+$ and dextran-$N^6$-(2-Aminoethyl)-$NAD^+$.

Polyethylene glycol-$N^6$-(2-Aminoethyl)-$NAD^+$ ($\overline{M}$ 10 000 and 20 000). To a stirred solution of 25 ml polyethylene glycol-$N^6$-(2-Aminoethyl)-NADH (0.15 mmol) at room temperature 1 ml 0.2 M potassium phosphate buffer, pH 7.2, and 10 ml 0.5 M acetaldehyde in $H_2O$ were added. After pH adjustment to 7.2 with 2 N HCl, 30 mg yeast alcohol dehydrogenase were added. The enzymatic oxidation was completed within 1 hour. The reaction mixture, adjusted to pH 5.5 with 2 N HCl, was poured in 500 ml methanol. After centrifugation a clear methanolic supernatant containing the polyethylene glycol-$N^6$-(2-Aminoethyl)-$NAD^+$ derivative was obtained. Most of the methanol was removed by flash evaporation and the aqueous solution was dialyzed at 4° C. against 3 times 2 liters of $H_2O$ at pH 5.0. 40 ml polyethylene glycol-$N^6$-(2-Aminoethyl)-$NAD^+$ was obtained containing 0.146 mmol coenzyme as determined by enzymatic reduction of a sample (yield 97%).

Dextran $N^6$-(2-Aminoethyl)-$NAD^+$ ($\overline{M}$ 40 000). Exactly the same reaction conditions as described above have been used for the enzymatic oxidation of dextran-$N^6$-(2-Aminoethyl)-NADH ($\overline{M}$ 40 000) with the highest NADH substitution to the corresponding $NAD^+$ derivative. After complete oxidation and adjustment to pH 5.5 the reaction solution was dialyzed at 4° C. against $H_2O$ (pH 5.0), yielding a preparation containing deactivated yeast alcohol dehydrogenase. Also in this case the loss of dextran-bound nucleotide was negligible.

Higher yields are possible if the purification of N(1)-(Aminoethyl)-$NAD^+$ is omitted and the lyophilized reaction mixture is directly used for the coupling. Taking in account the recycling of non-coupled N(1)-(Aminoethyl)-$NAD^+$ together with the by-product and an 1–4% loss during the Dimroth rearrangement the yield will be now in the range 80–84%.

The procedure for the reduction of polymer-bound N(1)-(Aminoethyl)-$NAD^+$ to polymer-bound N(1)-(Aminoethyl)-NADH has been slightly changed to milder conditions than those given in Example 1C: 2 minutes at 45° C. and then cooling directly to room temperature.

N.B. The biorex 70 column for the purification of N(1)-(Aminoethyl)-$NAD^+$ should have the dimension $70 \times 2.5$ cm.

Calculation yields

Dextran($\overline{M}$ 40 000)-$N^6$-(Aminoethyl)-NADH 73.5 μMol→72.2 μMol yield*=(72.2/73.5)×75% (yield after
N(1)-(Aminoethyl)-$NAD^+$ purification)=73.6%

Polyethyleneglycol($\overline{M}$ 10 000)-$N^6$-(Aminoethyl)-NADH 64.0 μMol→59.8 μMol yield*=(59.8/64.0)×75% (yield after
N(1)-(Aminoethyl)-$NAD^+$ purification=70.0%

*Assumed 100% recycling and reuse of non-coupled pure N(1)-(Aminoethyl)-$NAD^+$.

EXAMPLE 6

Conversion of NADP+ with ethyleneimine to N(1)-(Aminoethyl)-NADP+.

To 1 g NADP+ (1.27 mmol, Disodium salt, Boehringer), dissolved in 6 ml distilled $H_2O$, 200 µl ethyleneimine (4.22 mmol, Fluka) was slowly added, maintaining the pH at 4.5 with 0.2 M $HClO_4$. The reaction mixture (6.5 ml) was gently stirred in the dark at room temperature and the pH range kept at 4.3–4.7 by adding 0.2 M $HClO_4$. After 5 days the composition of the reaction mixture was (determined by TLC scanning as described before for NAD+ conversion):

17% NADP+ (not converted),
77% N(1)-(Aminoethyl)-NADP+
6% By-product (ninhydrine positive reaction ($-NH_2$ present), N(1)-alkyl spectral characteristics and coenzymatically active).

The reaction mixture, diluted 1:1 (v/v) with distilled $H_2O$, was poured into a centrifuge tube, containing 200 ml ice-cold ethanol. After centrifuging, the clear ethanolic supernatant was discarded and the precipitate washed once with the same volume of cold ethanol. The resulting white precipitate was dissolved in 50 ml distilled $H_2O$ and lyophilized. The lyophilized precipitate was directly used for the attachment to carboxylated polyethyleneglycol, since no satisfying procedure to obtain pure N(1)-(Aminoethyl)-$NADP^{30}$ by preparative ion exchange chromatography could yet be developed. (NADP+ (not converted) doesn't bind, but the main product N(1)-(Aminoethyl-NADP+ and the by-product do).

Attachment of N(1)-(Aminoethyl)-NADP+ to carboxylated polyethylene glycol

N(1)-(Aminoethyl)-NADP+ was attached to carboxylated polyethylene glycol ($\overline{M}$ 10 000) following the carbodiimide method as described by Cuatrecasas et al., J. Biol. Chem. 245, 3059 (1970). 0.3 g carboxylated polyethylene glycol ($\overline{M}$ 10 000) with about 0.06 mM terminal carboxyl groups was dissolved in 3.5 ml aqueous solution, containing 0.017 mmol NADP+, 0.077 mmol N(1)-(Aminoethyl)-NADP+ and 0.006 mmol by-product. After adjusting the pH to 4.8 with 1 N HCl, 80 mg 1-(3-dimethyl-aminopropyl)-3-ethylcarbodiimide-HCl (0.42 mmol) were added in 4 equal portions within 10 minutes. The pH was kept in the range 4.7–4.9 by adding 1 N HCl or 1 N NaOH during the first hour. After reacting 4 hours at room temperature the solution was kept for 15 hours at 4° C. The polyethylene glycol-NADP+ derivative was separated from low molecular weight compounds by gel filtration of the reaction mixture (4.5 ml) at 4° C. on A Sephadex G-50 (medium) column (1.5×100 cm), equilibrated against distilled $H_2O$. By flash evaporation the polyethylene glycol($\overline{M}$ 10 000)-N(1)-(Aminoethyl)-NADP+ fraction was concentrated to 2.8 mM (total 17.9 ml with 50.1 µMol coupled NADP+). Based on 0.06 mmol terminal carboxyl groups the coupling yield was 83.5%. The preparation showed an absorption maximum at 259 nm, with a shoulder in the range 300–310 nm at pH 11.5 due to the alkylated state of the N(1)-position of the adenine ring.

N.B. Concentration were determined spectrophotometrically at 259 nm using $\epsilon_{259} = 18\ 000\ M^{-1}cm^{-1}$. The polyethylene glycol($\overline{M}$ 10 000)-N(1)-(Aminoethyl)-NADP+ preparation will contain some minor amount of coupled by-product, which will be coenzymatically active too.

Synthesis of polyethylene glycol-N(1)-(Aminoethyl)-NADPH 14 ml polyethylene glycol($\overline{M}$ 10 000)-N(1)-(Aminoethyl)-NADP+ (concentration 2.8 mM with total 39 µMol coupled NADP+) were adjusted to pH 6.5 with 2 N NaOH and heated to 45° C. By stirring vigorously 280 mg $NaHCO_3$ (3.33 mmol) were quickly dissolved and 100 mg $Na_2S_2O_4$ (0.57 mmol) were then directly added in one charge. After a clear solution was obtained, the solution was stirred 2 min at 45° C. and cooled down in an ice-bath to room temperature. Then the pH was adjusted to 8.0 by adding 2 N NaOH and $O_2$ was bubbled through in a gentle stream for 7 min to oxidize the excess of reducing agent. 14.3 ml polyethylene glycol-($\overline{M}$ 10 000)-N(1)-(Aminoethyl)-NADPH were obtained with concentration 2.42 mM and a total of 34.6 µMol based on $\epsilon_{340} = 6220\ M^{-1}cm^{-1}$. This derivative showed a major absorption maximum at 259 nm with a second maximum at 340 nm, which indicates the presence of a reduced nicotinamide. At pH 11.5 an increased absorption in the range 300–310 nm points to the alkylated state of the N(1) position of the adenine ring. The ratio absorption at 259 nm/absorption at 340 nm = 2.8.

Synthesis of polyethylene glycol-$N^6$-(Aminoethyl)-NADPH 14.3 ml polyethylene glycol($\overline{M}$ 10 000)-N(1)-(Aminoethyl)-NADPH (concentration 2.42 mM with total 34.6 µMol coupled NADPH) were adjusted to pH 10.5 by adding 10 N NaOH and incubated at 70° C. for 135 min (Dimroth rearrangement). After gelfiltration at 4° C. on a Sephadex G-50 (medium) column (3.5×100 cm), equilibrated against 0.1 mM NaOH, the fraction with polyethylene glycol($\overline{M}$ 10 000)-$N^6$-(Aminoethyl)-NADPH was concentrated by flash evaporation to 14.5 ml, containing 33 µMol polyethylene glycol-bound $N^6$-(Aminoethyl)-NADPH with concentration 2.28 mM based on $\epsilon_{340} = 6220\ M^{-1}cm^{-1}$.

The major absorption maximum was at 267 nm with a second maximum at 340 nm. At pH = 11.5 no increase in absorption could be observed in the range 300–310 nm, which is indicative for the non-alkylated state of the N(1)-position of the adenine ring after Dimroth rearrangement. The ratio absorption at 267 nm/absorption at 340 nm = 4.1. By bovine liver glutamate dehydrogenase, which is also NADPH specific, the derivative could be enzymatically oxidized more than 95%. Taking in accound the recycling of non-coupled N(1)-(Aminoethyl)-NADP+ together with the coenzymatically active by-product and the loss after reduction and Dimroth rearrangement (39 µMol→33 µMol) the overall yield of this preparation is:

33/39×83% (conversion % of NADP+)=70.2%.

N.B. It is expected, that polyethylene glycol-$N^6$-(Aminoethyl)-NADP+ derivatives can be prepared enzymatically without any loss of NADP+.

EXAMPLE 7

Conversion of ATP with ethyleneimine to N(1)-(Aminoethyl)-ATP

To 10 g ATP (16.52 mmol di-sodium salt, Boehringer), dissolved in 20 ml $H_2O$, 2.0 ml ethyleneimine (42.2 mmol, Fluka) was slowly added, maintaining the pH at 4.5 with 70% HClO$_4$. The reaction mixture (25 ml) was gently stirred in the dark at room temperature and the pH range kept at 4.3–4.7 by adding 70% HClO$_4$. After 5 days the composition of the reaction mixture was (determined by TLC scanning as described before for NAD$^+$ conversion):

13% ATP

78% N(1)-(Aminoethyl)-ATP

9% By-product (ninhydrine positive reaction (—NH$_2$ present) and N(1)-alkyl spectral characteristics).

To obtain the reaction mixture in the lyophilized form the same procedure as described for NAD$^+$ conversion was followed (same vol/vol ratio). The lyophilized reaction mixture was directly used for the attachment to carboxylated polyethylene glycol. (ATP (not converted) doesn't bind, but the main product N(1)-(Aminoethyl)-ATP and the by-product do).

Attachment of N(1)-(Aminoethyl)-ATP to carboxylated polyethylene glycol.

N(1)-(Aminoethyl)-ATP was attached to carboxylated polyethylene glycol ($\overline{M}$ 10 000) following the carbodiimide method as described by Cuatrecasas et al., J. Biol. Chem. 245, 3059 (1970). 1 g carboxylated polyethylene glycol ($\overline{M}$ 10 000) with about 0.2 mmol terminal carboxyl groups was dissolved in 6 ml aqueous solution, containing 0.042 mmol ATP, 0.25 mmol N(1)-(Aminoethyl)-ATP and 0.029 mmol by-product. After adjusting the pH to 4.8 with 2 N HCl, 200 mg 1-(3-dimethylaminopropyl)-3-ethyl-carbodiimide-HCl (1.05 mmol) were added in 4 equal portions within 10 minutes. The pH was kept in the range 4.7–4.9 during the first hour. After reacting 4 hours at room temperature the solution as kept for 15 hours at 4° C. The polyethylene glycol-ATP derivative was separated from low molecular weight compounds by gel filtration of the reaction mixture (total 7 ml) at 4° C. on a Sephadex G-50 (medium) column (3×100 cm), equilibrated against distilled H$_2$O. By flash evaporation the polyethylene glycol($\overline{M}$ 10 000)-N(1)-(Aminoethyl)-ATP fraction was concentrated to 3.54 mM (total 45 ml with 160 μMol coupled ATP). Based on 0.2 mmol terminal carboxyl groups the coupling yield was 80%. The preparation showed an absorption maximum at 259 nm with a shoulder in the range 300–310 nm at pH 11.5 due to the alkylated state of the N(1) position of the adenine ring.

N.B. Concentrations were determined spectrophotometrically at 259 nm using $\epsilon_{259}=15\,400$ M$^{-1}$cm$^{-1}$.

The polyethylene glycol($\overline{M}$ 10 000)-N(1)-(Aminoethyl)-ATP preparation will contain some minor amount of coupled by-product.

Synthesis of polyethylene glycol-N$^6$-(Aminoethyl)-ATP 10 ml polyethylene glycol ($\overline{M}$ 10 000)-N(1)-(Aminoethyl)-ATP (concentration 3.54 mM with a total of 35.4 μMol bound ATP) were adjusted to pH 11.0 by adding 10 N NaOH and incubated during 4 days at 25° C. After adjusting the pH to 5 by adding 2 N HCl, 10.7 ml polyethylene glycol($\overline{M}$ 10 000)-N$^6$-(Aminoethyl)-ATP was obtained with still a total of 35.4 μMol bound nucleotide (concentration 3.3 mM) since:

1. no free nucleotide could be detected by gel filtration of 100 μl at 4° C. on a Sephadex G-50 (medium) colum (0.5×60 cm), equilibrated against 1% HCl.
2. Compared to 3.3 mM solutions of ATP and polyethylene glycol($\overline{M}$ 10 000)-N(1)-(Aminoethyl)-ATP (based on $\epsilon_{259}=15\,400$ M$^{-1}$cm$^{-1}$) the same concentration was found in the preparation after Dimroth rearrangement by the hexokinase/glucose-6-phosphate dehydrogenase assay (same total increase in absorption at 340 nm due to NADPH formation):

ATP + Glucose $\xrightarrow{\text{HK}}$ Glucose-6-Phosphate + ADP

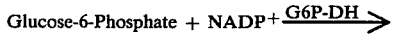

Glucose-6-Phosphate + NADP$^+$ $\xrightarrow{\text{G6P-DH}}$

Gluconate-6-Phosphate + NADPH + H$^+$

The polyethylene glycol($\overline{M}$ 10 000)-N$^6$-(Aminoethyl)-ATP derivative showed a maximum at 267 nm with no shoulder in the range 300–310 nm at pH 11.5, which points to the non-alkylated state of the N(1) position of the adenine ring after Dimroth rearrangement. From the spectra before and after Dimroth rearrangement $\epsilon_{267}=19\,500$ M$^{-1}$cm$^{-1}$ was calculated. Taking in account the recycling of non-coupled N(1)-(Aminoethyl)-ATP and the by-product and no loss during the rearrangement the overall yield will be equal to the % of conversion of ATP (87%).

EXAMPLE 8

Conversion of AMP with ethyleneimine to N(1)-(Aminoethyl)-AMP

To 10 g AMP (27.4 mmol free acid, Boehringer), dissolved in 35 ml distilled H$_2$O by titrating with 10% NaOH, 2.6 ml ethyleneimine (55 mmol, Fluka) was slowly added, maintaining the pH at 4.5 with 70% HClO$_4$. The reaction mixture (40 ml) was gently stirred in the dark at room temperature and the pH range kept at 4.3–4.7 by adding 70% HClO$_4$. After 5 days the composition of the reaction mixture was (determined by TLC scanning as described for NAD$^+$ conversion):

11% AMP (not converted)

81% N(1)-(Aminoethyl)-AMP

8% By-product (ninhydrine positive reaction (—NH$_2$ present) and N(1)-alkyl spectral characteristics).

To obtain the reaction mixture in the lyophilized form the same procedure was followed as described for NAD+conversion (some vol/vol ratio). The lyophilized reaction mixture was directly used for the attachment to carboxylated polyethylene glycol. (AMP (not converted) doesn't bind, but the main product N(1)-(Aminoethyl)-AMP and the by-product do).

Attachment of N(1)-(Aminoethyl)-AMP to carboxylated polyethylene glycol

N(1)-(Aminoethyl)-AMP was attached to carboxylated polyethylene glycol ($\overline{M}$ 10 000) following the carbodiimide method as described by Cuatrecasas et al., J. Biol. Chem. 245, 3059 (1970). 1 g carboxylated polyethylene glycol ($\overline{M}$ 10 000) with about 0.2 mmol terminal carboxyl groups was dissolved in 6 ml aqueous solution, containing 0.05 mmol AMP, 0.23 mmol N(1)-(Aminoethyl)-AMP and 0.018 mmol by-product. After adjusting the pH to 4.8 with 2 N HCl, 200 mg 1-(3-dimethylaminopropyl)-3-ethyl-carbodiimide-HCL (1.05 mmol) were added in 4 equal portions within 10 minutes. The pH was kept in the range 4.7–4.9 during the first hour. After reacting 4 hours at room temperature the solution was kept for 15 hours at 4° C. The polyethylene glycol-AMP derivative was separated from low molecular weight compounds by gel filtration of the reaction mixture (total 6.8 ml) at 4° C. on a Sephadex G-50 (medium) column (3×100 cm), equilibrated against distilled H$_2$O.

By flash evaporation the polyethylene glycol ($\overline{M}$ 10 000)-N(1)-(Aminoethyl)-AMP fraction was concentrated to 3.46 mM (total 50 ml with 173 μMol coupled AMP). Based on 0.2 mmol terminal carboxyl groups the coupling yield was 86.6%. The preparation showed an absorption maximum at 259 nm with a shoulder in the range 300–310 nm at 11.5 due to the alkylated state of the N(1) position of the adenine ring.

N.B. Concentrations were determined spectrophotometrically at 259 nm using $\epsilon_{259}$ 15 400 $M^{-1}cm^{-1}$. The polyethylene glycol($\overline{M}$ 10 000)-N (1)-Aminoethyl)-AMP preparation will contain some minor amount of coupled by-product.

Synthesis of polyethylene glycol-N$^6$-(Aminoethyl)-AMP 10 ml polyethylene glycol($\overline{M}$ 10 000)-N(1)-(Aminoethyl)-AMP (concentration 3.46 mM with a total of 34.6 μMol coupled AMP) was adjusted to pH 11.0 by adding 10 N NaOH and incubated during 4 days at 25° C. (Dimroth rearrangement). After adjusting the pH to 5 by adding 2 N HCl 10.6 ml polyethylene glycol($\overline{M}$ 10 000)-N$^6$-(Aminoethyl)-AMP were obtained with still a total of 34.6 μMol (concentration 3.26 mM ), since no free nucleotide could be detected by gel filtration of 100 μl at 4° C. on a Sephadex G-50 (medium) column (0.5×60 cm), equilibrated with 1% HCl. It is assumed that AMP bound to polyethylene glycol will be stable at the described rearrangement conditions, since the much more labile ATP bound to polyethylene glycol remains also intact at the same conditions. The polyethylene glycol($\overline{M}$ 10 000)-N$^6$-(Aminoethyl)-AMP derivative showed a maximum at 267 nm but no shoulder in the range 300–310 nm at pH 11.5, which points to the non-alkylated state of the N(1) position of the adenine ring after Dimroth rearrangement. From the spectra before and after Dimroth rearrangement $\epsilon_{267}=17\ 500\ M^{-1}cm^{-1}$ was calculated.

Taking in account the recycling of non-coupled N(1)-(Aminoethyl)-AMP and the by-product and no loss during the rearrangement the overall yield will equal to the % of the conversion of AMP (89%).

EXAMPLES 9 TO 10

Polyethylene glycol-N(1)-(2-Aminoethyl)-NAD+

10 g carboxylated polyethylene glycol ($\overline{M}$ 10 000) with approximately 2 mmol terminal carboxyl groups were dissolved in a solution of 2 mmol purified N(1)-(2-Aminoethyl)-NAD+ in 25 ml distilled water. After adjusting the pH to 4.8 with 2 N HCl, 1.15 g 1-(3-dimethyl-aminopropyl)-3-ethyl-carbodiimide-HCl (6 mmol) were added in 4 equal portions within 10 minutes. The pH was adjusted to 4.8 by either adding 2 N HCl or 2 N NaOH during the first hour of the reaction. In case of carboxylated polyethylene glycol ($\overline{M}$ 20 000) 20 g were dissolved in a solution of 2 mmol N(1)-(2-Aminoethyl)-NAD+ in 45 ml distilled water, before adding the same amount of carbodiimide as described above. After reacting 4 h at room temperature the solution was kept for 15 h at 4° C. The polyethylene glycol-N(1)-(2-Aminoethyl)-NAD+ derivatives were separated from low molecular weight compounds by gel filtration of the reaction mixture on a preparative Sephadex G-50 (medium) column (5+120 cm), equilibrated against distilled H$_2$O. By flash evaporation the polyethylene glycol-N(1)-(2-Aminoethyl)-NAD+ fractions were concentrated to 12 mM and adjusted to pH 5.0 with 2 N NaOH, resulting in 151 ml polyethylene glycol-N(1)-(2-Aminoethyl)-NAD+ (E,ovs/M/ 10 000) and 145 ml polyethylene glycol-N(1)-(2-Aminoethyl)-NAD+ ($\overline{M}$ 20 000) with coupling yields of 91 and 87%, respectively.

Polyethylene glycol-N$^6$-(2-Aminoethyl)-NADH ($\overline{M}$ 10 000 and 20 000)

150 ml polyethylene glycol-N(1)-(2-Aminoethyl)-NAD+ (1.8 mmol) were adjusted to pH 6.5 with 5 N NaOH and heated to 45° C. By stirring vigorously 7.5 g NaHCO$_3$ (89.2 mmol) were quickly dissolved and 2 g Na$_2$S$_2$O$_4$ (11.5 mmol) were then directly added in one charge. After a clear solution was obtained, the solution was stirred 2 min at 45° C. and cooled down in an icebath to room temperature. Then the pH was adjusted from 7.3 to 8.0 by adding 10 N NaOH and O$_2$ was bubbled through in a gentle stream for 7 min to oxidize the excess of reducing agent. By adding 10 N NaOH the polyethylene glycol-N(1)-(2-Aminoethyl)-NADH solution was adjusted to pH 11 and incubated with stirring for 105 min at 70° C. to carry out the Dimroth rearrangement. The resulting polyethylene glycol-N$^6$-(2-Aminoethyl)-NADH solution was then exhaustively dialyzed at 4° C. against 6 times 5 l H$_2$O, adjusted to pH 10 with 1 N NaOH, to remove low molecular weight compounds.

Polyethylene glycol-N$^6$-(2-Aminoethyl)-NAD+ ($\overline{M}$ 10 000 and 20 000)

To a stirred solution of 25 ml polyethylene glycol-N$^6$-(2-Aminoethyl)-NADH (0.15 mmol) at room temperature 1 ml 0.2 M potassium phosphate buffer, pH 7.2, and 10 ml 0.5 M acetaldehyde in H$_2$O were added. After pH adjustment to 7.2 with 2 N HCl, 30 mg yeast alcohol dehydrogenase were added. The enzymatic oxidation was completed within 1 hour. The reaction mixture, adjusted to pH 5.5 with 2 N HCl, was poured in 500 ml methanol. After centrifugation a clear methanolic supernatant containing the polyethylene glycol-N$^6$-(2-Aminoethyl)-NAD+ derivative was obtained. Most of the methanol was removed by flash evaporation and the aqueous solution was dialyzed at 4° C. against 3 times 2 l H$_2$O at pH 5.0. 40 ml polyethylene glycol-N$^6$-(2-Aminoethyl)-NAD+ were obtained containing 0.146 mmol coenzyme as determined by enzymatic reduction of a sample (yield 97%).

EXAMPLES 11 TO 13

Dextran-N(1)-(2-Aminoethyl)-NAD+

2 g Carboxymethyl-dextran (E,ovs/M/ 40 000, 150 000 and 500 000) was approximately 3.6 mmol carboxymethyl groups were dissolved in 60 ml distilled H$_2$O together with 1.32 mmol N(1)-(2-Aminoethyl)-NAD+. After adjustment of the pH to 4.8 with 2 N HCl, 1.3 g 1-(3-dimethylaminopropyl)-3-ethyl-carbodiimide HCl (6.8 mmol) were added in 4 equal portions within 10 minutes. During the first hour of the reaction the pH was kept at 4.8 by adding 2 N HCL or 2 N NaOH. After reacting 4 h at room temperature the reactin mixture was kept for 15 h at 4° C., the dextran N(1)-(2-Aminoethyl)-NAD+ derivatives were separated from low molecular weight compounds by gel filtration of the reaction mixture on a preparative Sephadex G-50 (medium) column (5×120 cm), equilibrated against 0.02% KCl. By flash evaporation the dextran-N(1)-(2-Aminoethyl)-NAD+ fractions were concentrated to 10 mM and adjusted to pH 5.0 resulting in 55 ml dextran-N(1)-(2-

Aminoethyl)-NAD+ ($\overline{M}$ 40 000), 57 ml dextran-N(1)-(2-Aminoethyl)-NAD+ ($\overline{M}$ 150 000) and 53 ml dextran-N(1)-(2-Aminoethyl)-NAD+ ($\overline{M}$ 500 000) with coupling yields of respectively 41.5, 43, and 40%. About 1 N(1)-(Aminoethyl)-NAD+ molecule pro 20 anhydroglucose monomers was present. Less substituted dextran-N(1)-(2-Aminoethyl)-NAD+ could be obtained by decreasing the amount of nucleotide and carbodiimide in the reaction mixture: By using 0.7 mmol N(1)-(2-Aminoethyl)-NAD+ and 3 mmol 1-(3-dimethylaminopropyl)-3-ethylcarbodiimide-HCl dextran-N(1)-(2-Aminoethyl)-NAD+ ($\overline{M}$ 40 000) was prepared as described above with about 1 N(1)-(2-Aminoethyl)-NAD+ molecule per 40 anhydroglucose monomer units.

Dextran $N^6$-(2-Aminoethyl)-NADH ($\overline{M}$ 40 000, 150 000, and 500 000)

40 ml dextran-N(1)-(2-Aminoethyl)-NAD+ (0.4 mmol) were adjusted to pH 6.5 with 10 N NaOH and heated to 45° C. Then successively 1.8 g NaHCO$_3$ (21.4 mmol) and 0.47 g Na$_2$S$_2$O$_4$ (2.68 mmol) were dissolved. The reduction to dextran-N(1)-(2-Aminoethyl)-NADH, the rearrangement to dextran-$N^6$-(2-Aminoethyl)-NADH and the dialysis were carried out in exactly the same way as described above for the polyethylene glycol derivatives.

By spectrophotometric measurement at 340 nm the polyethylene glycol- and dextran-NADH preparations were compared before and after Dimroth rearrangement and dialysis. In all cases losses in the range of 3-4% were observed.

Dextran $N^6$-(2-Aminoethyl)-NAD+ ($\overline{M}$ 40 000)

Exactly the same reaction conditions as described above have been used for the enzymatic oxidation of dextran-$N^6$-(2-Aminoethyl)-NADH ($\overline{M}$ 40,000) with the highest NADH substitution to the corresponding NAD+ derivative. After complete oxidation and adjustment to pH 5.5 the reaction solution was dialyzed at 4° C. against H$_2$O (pH 5.0), yielding a preparation containing inactivated yeast alcohol dehydrogenase. Also in this case the loss of dextran-bound nucleotide was negligible.

Dextran $N^6$-(2-Aminoethyl)-NAD+ ($\overline{M}$ 150 000 and 500 000)

The enzymatic oxidation of dextran-$N^6$-(2-Aminoethyl)-NADH with $\overline{M}$ 40 000 was repeated with the same result for the corresponding compounds with $\overline{M}$ 150 000 and 500 000, resp. Macromolecular weight enlarged ADP.

ADP hasn't been coupled yet to polyethylene glycol analogous to the procedure as described for AMP and ATP.

It can be expected that polyethylene glycol-$N^6$-(Aminoethyl)-ADP derivatives might be obtained with overall yields in the same range (>85%) since the stability of ADP is comparable to ATP.

Remark: It is also possible to designate position 1 of the adenine ring system as position N(1).

I claim:

1. A process for the production of an adenine ring system containing co-enzymes bound to a macromolecular carrier consisting essentially of:
   (a) reacting a co-enzyme selected from the group consisting of AMP, ADP, ATP, NAD+ and NADP, said co-enzyme having an adenine ring system substituted by an alkylene chain in the 1 position, said alkylene chain containing from 1 to 3 carbon atoms and a functional group capable of reacting with a macromolecular carrier selected from the group consisting of carboxyl, hydroxyl, —NH$_2$ and vinyl, with a macro-molecular carrier selected from the group consisting of dextrans, polyetherpolyols, polyethyleneimines, polyacrylamides and poly-(methylvinylether/maleic acid anhydride), said carrier having groups capable of reacting with said functional group,
   (b) subjecting said alkylated co-enzyme bound to said macro-molecular carrier to a Dimroth rearrangement into the $N^6$-form of substitution, and
   (c) recovering said $N^6$-substituted co-enzyme bound to said macro-molecular carrier.

2. The process of claim 1 wherein said groups capable of reacting with said functional groups on said carrier are carboxyl groups.

3. The process of claim 1 wherein said functional group capable of reacting with a macro-molecular carrier is NH$_2$.

* * * * *